(12) United States Patent
Kiene

(10) Patent No.: US 7,566,366 B2
(45) Date of Patent: Jul. 28, 2009

(54) COVERSLIPPING MACHINE

(75) Inventor: Uwe Kiene, Eppelheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 365 days.

(21) Appl. No.: 11/380,758

(22) Filed: Apr. 28, 2006

(65) Prior Publication Data

US 2006/0243199 A1    Nov. 2, 2006

(30) Foreign Application Priority Data

Apr. 29, 2005   (DE) .................. 10 2005 020 426

(51) Int. Cl.
*B05C 5/02* (2006.01)

(52) U.S. Cl. ............... 118/302; 15/56; 422/63; 422/64; 422/99; 422/100; 436/180; 134/169 C; 134/167 C; 134/166 C

(58) Field of Classification Search ........... 118/302; 134/169 C, 167 C, 166 C; 15/56; 422/63, 422/64, 99, 100; 436/180

See application file for complete search history.

(56) References Cited

U.S. PATENT DOCUMENTS 2,899,929 A * 8/1959 Monroe .................. 118/302
2004/0250842 A1* 12/2004 Adams et al. ........... 134/169 C

FOREIGN PATENT DOCUMENTS

| AU | 9218248 A | * | 6/1992 |
| DE | 29514506 U1 | | 9/1995 |
| JP | 64-56164 | * | 3/1989 |

OTHER PUBLICATIONS

Leica Microsystems Nussloch GMBH (Nussloch, Germany), "Leica CV5030 Glass Coverslipper for Histology and Cytology", Brochure No. 0707-2-0-101, Sep. 2002.

* cited by examiner

*Primary Examiner*—Laura Edwards
(74) *Attorney, Agent, or Firm*—Hodgson Russ LLP

(57) ABSTRACT

A coverslipping machine (1) for applying coverslipping agent and a coverslip onto a specimen slide is described. A hollow needle (2), which is embodied to be movable via a guide (4) into a working position for application of the coverslipping agent from a reservoir (3) onto the specimen slide, is additionally movable via the guide (4) into a parked position. A cleaning device (5) for the hollow needle (2) is arranged at the parked position.

7 Claims, 3 Drawing Sheets

COVERSLIPPING MACHINE

CROSS REFERENCE TO RELATED APPLICATIONS

This application claims priority of the German patent application 10 2005 020 426.0 filed Apr. 29, 2005, which is incorporated by reference herein.

FIELD OF THE INVENTION

The invention concerns a coverslipping machine of a type having a hollow needle for applying coverslipping agent onto a specimen slide.

BACKGROUND OF THE INVENTION

Coverslipping of the specimen slide represents the last working step in the preparation of specimens for subsequent microscopic investigation. Once the specimen has been prepared, it is arranged on the specimen slide and covered with a very thin coverslip. To protect the specimen, the coverslip is joined to the specimen slide using a coverslipping agent, usually a solvent-containing adhesive. Coverslipping can be accomplished both manually and with the use of automatically operating coverslipping machines.

DE 295 14 506 U1 discloses a coverslipping machine of this kind in which the specimen slides are arranged on a rotatably supported plate. A nozzle or hollow needle for applying the coverslipping agent is arranged in stationary fashion at one point on the machine. After application of the coverslipping agent, a coverslip is transported by means of a vacuum suction device, via a rotatably supported transport arm embodied in vertically adjustable fashion, to the specimen slide and placed thereon.

When the coverslipping machine is not being used, or during downtimes, the risk exists that the coverslipping agent may dry out in the hollow needle and thus clog it. Depending on the ambient temperature, drying of the coverslipping agent can occur after only a few minutes.

To eliminate this risk, coverslipping machines that have been described are provided with a separate container having solvent, into which the entire hollow-needle holder can be manually introduced. This obviously requires that a holding screw in the holding apparatus of the hollow needle holder must first have been loosened, so that the hollow needle holder is then pulled out of the holding apparatus and placed in the solvent container.

This arrangement reliably protects the hollow needle from drying out. The risk nevertheless still exists that introduction of the hollow needle into the solvent container will be overlooked or be performed only after a delay, and the coverslipping agent will have at least partly dried out so that uniform coverslipping agent application is not guaranteed.

Dried-out or partly dried-out coverslipping agent, however, inevitably results in damaged specimens, so that the laboriously prepared specimens become unusable.

An automatically operating coverslipping machine having a gripper system is known from the document "Leica DV5030, 'The ideal glass coverslipper for histology and cytology,' order no. 0707-2-1-101, 09/02, Sep. 2002." The gripper system of the coverslipping machine is designed to take the specimen slides directly out of the transport baskets and deliver them to the coverslipping position. Here as well, the coverslipping agent is applied onto the specimen slide from a reservoir and a hollow needle (dispenser valve). For that purpose, the hollow needle is attached via a needle holder, in linearly movable fashion, to a guide arm.

In the event of an interruption or during work breaks, here again the needle holder having the hollow needle must be moved manually from the guide arm into a holding apparatus having a solvent container. The needle holder can is in this case easily be removed from the guide arm by way of orifices and guide rods and positioned in the holding apparatus of the solvent container. The problem nevertheless still exists that introduction of the hollow needle into the solvent container may be overlooked or performed only after a delay.

The Leica CV5030 unit presented here can be operated in standalone fashion or, with the Leica ST5020 Multistainer, as a combination staining and coverslipping system that operates completely automatically. It is of course necessary to ensure in this context that, if the "material flow" is not continuous, drying out of the hollow needle is ruled out.

SUMMARY OF THE INVENTION

It is therefore the object of the present invention to ensure continuous operation of a coverslipping machine, and to enable effortless resumption of operation even in a context of downtimes.

The invention is characterized in that the hollow needle is embodied to be additionally movable via the guide into a parked position, and that a cleaning device for the hollow needle is arranged at the parked position. This ensures that during coverslipping machine downtimes, the hollow needle is movable via the existing guide into a cleaning device.

In a refinement of the invention, the cleaning device comprises a container having solvent and a brush. The result of this is that the flexible bristles of the brush create a contact with the hollow needle, thus ensuring reliable solvent transport.

In a further embodiment of the invention, at least one felt pad is provided for transporting the solvent from the bottom of the container to the bristles of the brush. The felt pads ensure reliable solvent transport to the brush even if the solvent level within the container is low.

In a refinement of the invention, a cover is associated with the container, and an opening for insertion of the hollow needle is provided in the cover. This configuration prevents the container from prematurely drying out, and substantially extends service life.

In a further embodiment of the invention, the opening in the cover of the container is slit-shaped.

In an advantageous refinement of the invention, a holder is associated with the brush, and the holder is arranged removably in the container. With this configuration, the brush in the container is easily replaceable, so that a worn or damaged brush does not require complex reconfigurations.

In a further embodiment of the invention, the holder is configured symmetrically, and the brush is also insertable into the container, via the holder, having been rotated 180 degrees. This ensures that a brush that is worn on one side can continue to be used by being rotated.

In a refinement of the invention, the container comprises a mounting bracket for securing the container in the coverslipping machine. With the mounting bracket, the container can easily be secured in the coverslipping machine so that easy retrofitting of the cleaning device is also possible.

The invention will be explained in more detail with reference to an exemplifying embodiment with the aid of the schematic drawings, in which FIG. 1 is a perspective view of a coverslipping machine formed in accordance with an embodiment of the present invention;

DETAILED DESCRIPTION OF THE INVENTION

Figure 1:
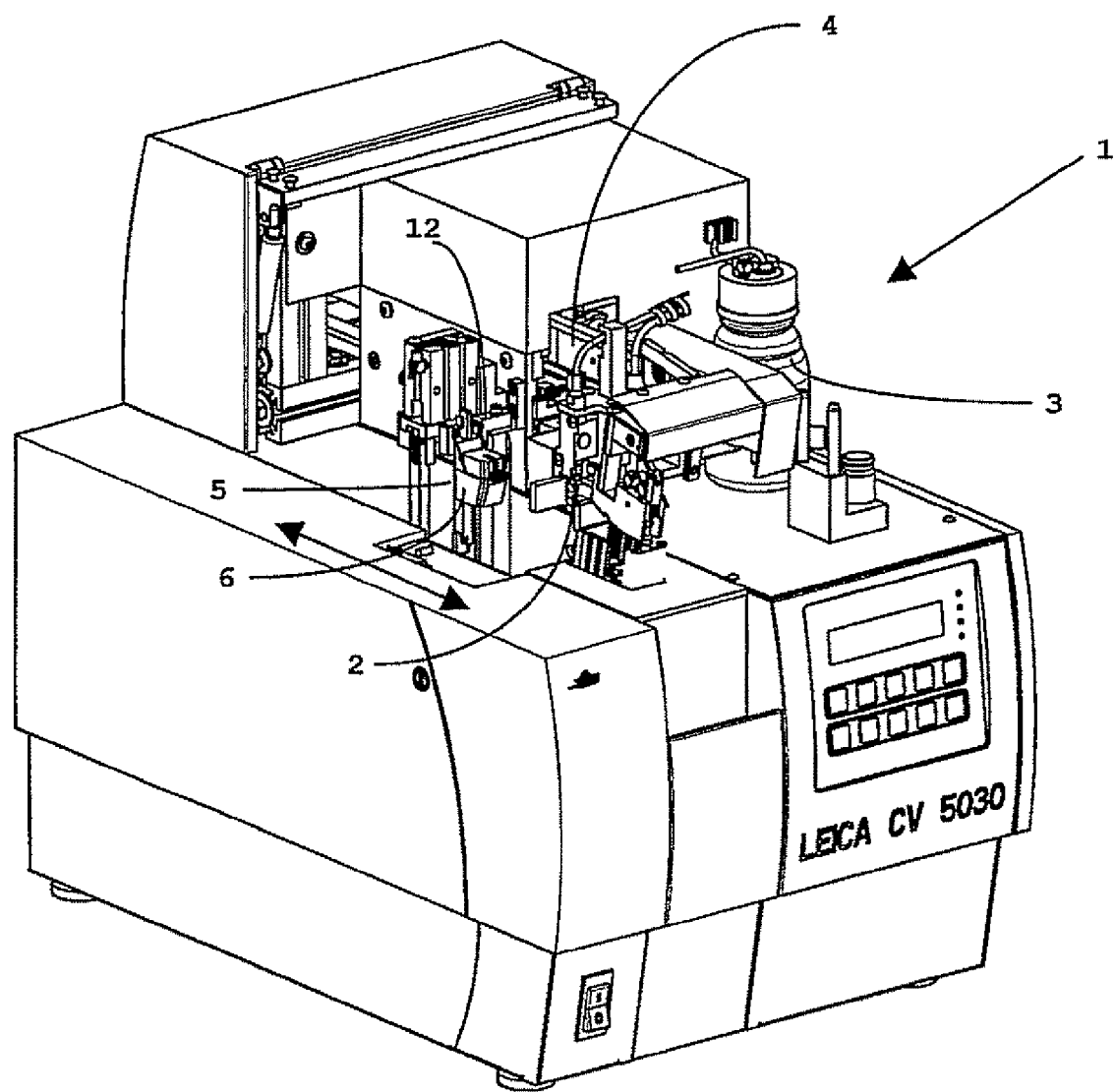

FIG. 1 is a view of coverslipping machine 1 having a hollow needle 2 that applies coverslipping agent from a reservoir 3 onto a specimen slide (not depicted here). Hollow needle 2 is arranged on a guide 4 and is embodied to be movable in the double-arrow direction along that guide 4.

A cleaning device 5 having a container 6 and a cover 9 is secured on coverslipping machine 1 via a mounting bracket 12.

Hollow needle 2 is embodied movably along guide 4 into a working position for application of the coverslipping agent, and into a parked position for cleaning. Arranged at the parked position is cleaning device 5 into which hollow needle 2 is introduced by the guide.

Figure 2:
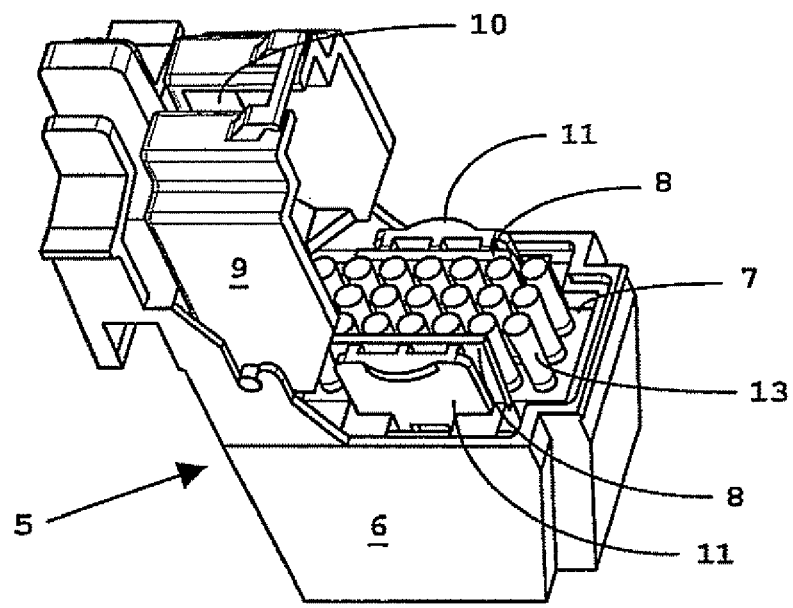
FIG. 2 is a perspective view of a cleaning device of the coverslipping machine shown in FIG. 1.

FIG. 2 shows cleaning device 5 having container 6 and cover 9 that comprises a slit-shaped opening 10. Arranged in container 6 is a brush 7 that comprises a plurality of bristles 13. Brush 7 is inserted via a holder 11 into container 6. Clamped between holder 11 and brush 7 is a surrounding felt pad 8 that extends to the bottom of container 6 and ensures reliable solvent transport to bristles 13 of brush 7 even when the solvent level is low.

In the working position, cover 9 is closed so that the solvent can escape only through the narrow slit-shaped opening 10 in cover 9. The hollow needle is introduced into cleaning device 5 through opening 10.

Figure 3:
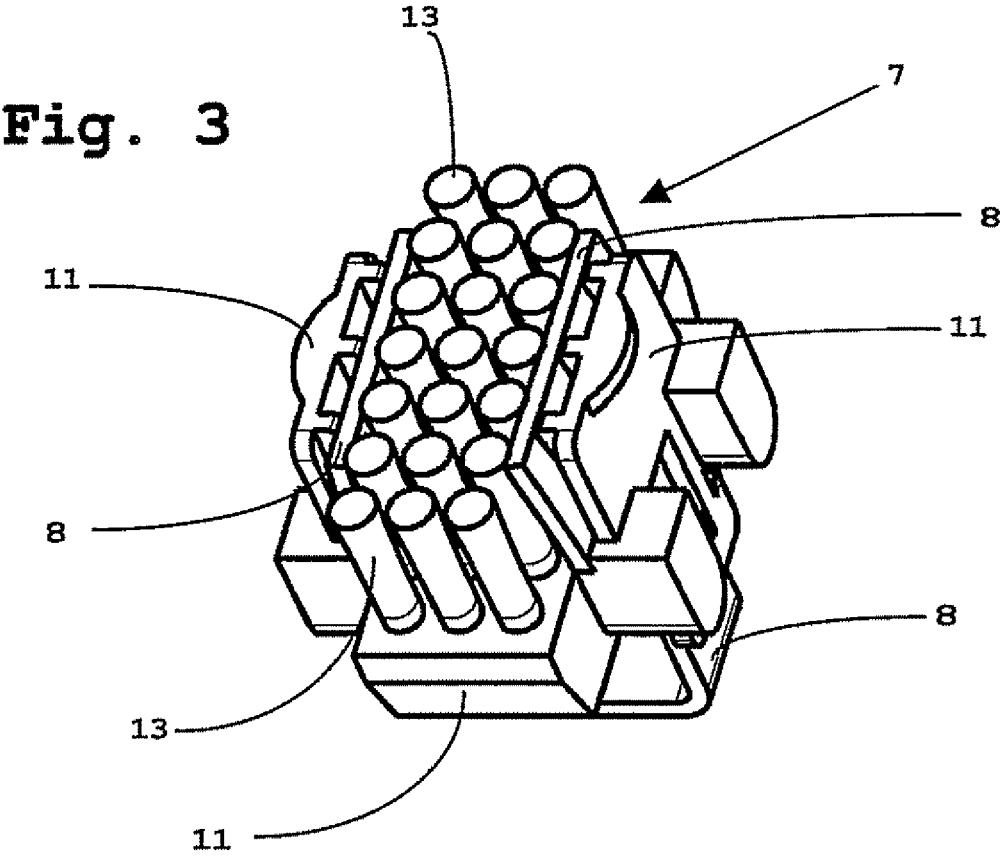
FIG. 3 is a perspective view of a holder of the cleaning device with brush.

FIG. 3 is a view of brush 7 with bristles 13, holder 11, and surrounding felt pad 8. Holder 7 is symmetrically constructed, and can also be inserted into container 6 having been rotated 180 degrees.

Figure 4:
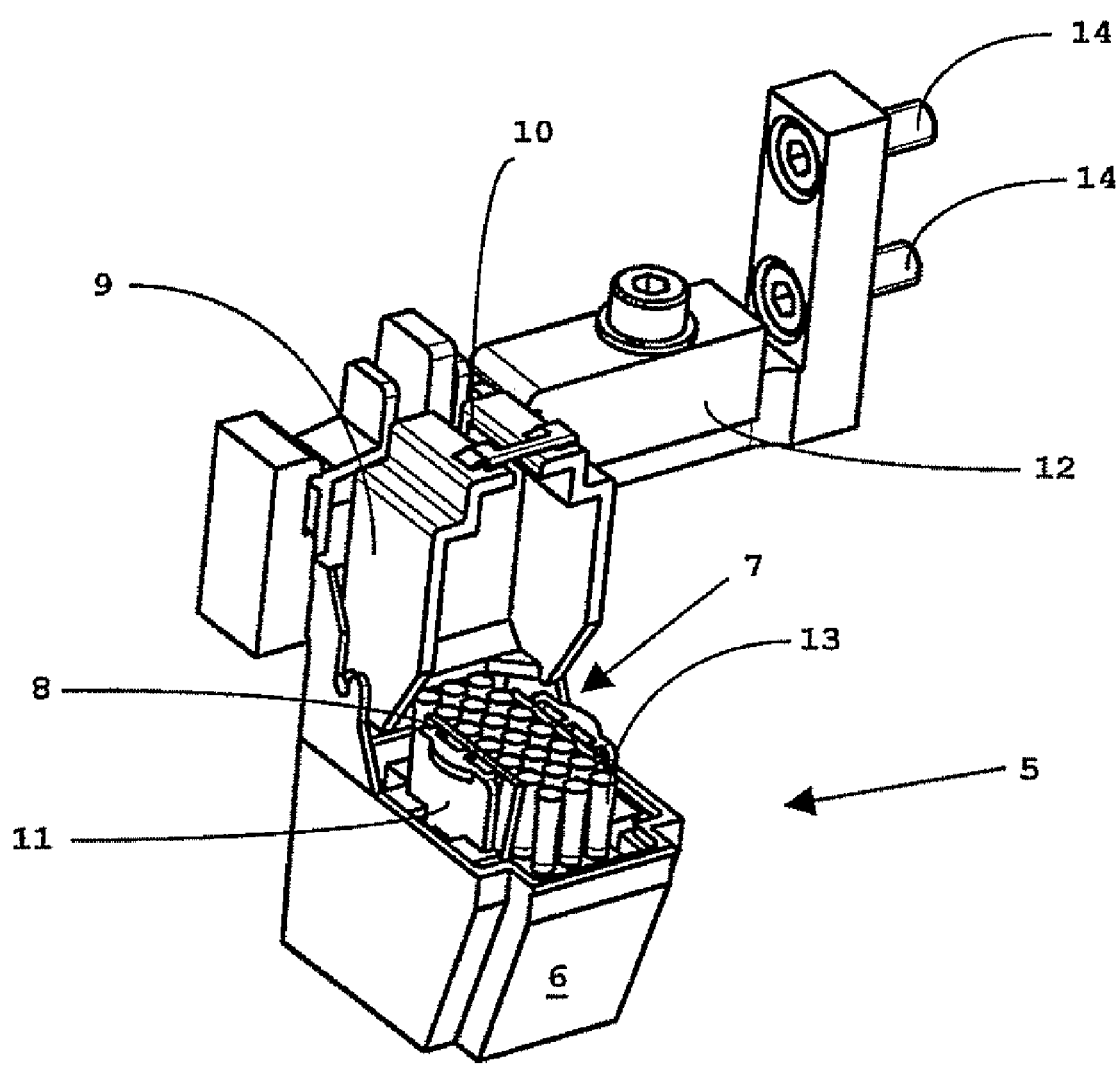
FIG. 4 is a perspective view of the cleaning device with a mounting bracket.

FIG. 4 is a view of cleaning device 5 with container 6, cover 9, and brush 7 arranged in cover 6. A mounting bracket 12 that carries two securing screws 14 is associated with container 6. Cleaning device 5 is secured in the coverslipping machine via securing screws 14.

PARTS LIST

1 Coverslipping machine
2 Hollow needle
3 Reservoir
4 Guide of (2)
5 Cleaning device
6 Container of (5)
7 Brush
8 Felt pad
9 Cover of (6)
10 Opening in (9)
11 Holder of (7)
12 Mounting bracket
13 Bristles of (7)
14 Securing screws

What is claimed is:

1. A coverslipping machine, comprising:
   a reservoir for holding coverslipping agent;
   a hollow needle in communication with the reservoir;
   a cleaning device, wherein the cleaning device includes a brush having bristles and a container for holding solvent; and
   a guide on which the needle is mounted for travel between a working position wherein the needle applies coverslipping agent onto a specimen slide and a parked position wherein the needle is received by the cleaning device;
   wherein the cleaning device further includes a felt pad arranged for transporting solvent from a bottom of the container to the bristles of the brush.

2. The coverslipping machine according to claim 1, further comprising a mounting bracket for securing the container in the coverslipping machine.

3. A coverslipping machine, comprising:
   a reservoir for holding coverslipping agent;
   a hollow needle in communication with the reservoir;
   a cleaning device, wherein the cleaning device includes a brush having bristles and a container for holding solvent; and
   a guide on which the needle is mounted for travel between a working position wherein the needle applies coverslipping agent onto a specimen slide and a parked position wherein the needle is received by the cleaning device;
   wherein the cleaning device further includes a cover associated with the container, the cover having an opening through which the needle is received into the cleaning device.

4. The coverslipping machine according to claim 3, wherein the opening is slit-shaped.

5. The coverslipping machine according to claim 3, further comprising a mounting bracket for securing the container in the coverslipping machine.

6. A coverslipping machine, comprising:
   a reservoir for holding coverslipping agent;
   a hollow needle in communication with the reservoir;
   a cleaning device, wherein the cleaning device includes a brush having bristles and a container for holding solvent; and
   a guide on which the needle is mounted for travel between a working position wherein the needle applies coverslipping agent onto a specimen slide and a parked position wherein the needle is received by the cleaning device;
   wherein the cleaning device further includes a holder removably received by the container for holding the brush;
   wherein the holder is configured symmetrically so that the brush can be rotated by 180 degrees with respect to the container and the cover.

7. The coverslipping machine according to claim 6, further comprising a mounting bracket for securing the container in the coverslipping machine.

* * * * *